US005098525A

United States Patent [19]

Lorenzoni et al.

[11] Patent Number: 5,098,525

[45] Date of Patent: Mar. 24, 1992

[54] PROCESS FOR DISPOSING OF RESIDUES DERIVING FROM THE SYNTHESIS OF CHLORINATED HYDROCARBONS

[75] Inventors: Loreno Lorenzoni, Porto Torres; Giuseppe Messina, Alghero; Vittorio Bruzzi, Milan; Salvatore Simula, Ittiri, all of Italy

[73] Assignee: Enichem Anic, S.p.A., Palermo, Italy

[21] Appl. No.: 534,183

[22] Filed: Jun. 6, 1990

[30] Foreign Application Priority Data

Jun. 8, 1989 [IT] Italy ............................ 20817 A/89

[51] Int. Cl.[5] .......................... B01D 3/34; C07C 17/38

[52] U.S. Cl. .......................................... 203/38; 203/47; 203/63; 203/80; 570/238

[58] Field of Search .................. 203/38, 63, DIG. 23, 203/75, 77, 78, 80, 81, 47, 71; 570/238

[56] References Cited

U.S. PATENT DOCUMENTS 3,947,508 3/1976 Correia et al. ........................ 203/38
4,024,049 5/1977 Shell et al. .............................. 203/6
4,065,267 12/1977 Ladage et al. ......................... 203/38
4,271,315 6/1981 Cywinski .............................. 203/38
4,339,237 7/1982 Wang et al. ............................. 8/917
4,412,086 10/1983 Beard, Jr. et al. .................... 203/38

FOREIGN PATENT DOCUMENTS 1228232 7/1967 Fed. Rep. of Germany .
1555084 11/1979 United Kingdom .

*Primary Examiner*—Wilbur Bascomb, Jr.
*Attorney, Agent, or Firm*—Birch, Stewart, Kolasch & Birch

[57] ABSTRACT

The disposal of chlorinated pitches is carried out by a process which employs two treatments with an alcohol, which are carried out in cascade.

Such treatments cause the precipitation of the suspended matter to take place. This is then caused to settle, and is separated and pyrolized, while the supernatant is distilled in order to separate the alcohol, which is recycled back to the process, from other organic components, which are sent to further uses.

10 Claims, No Drawings

PROCESS FOR DISPOSING OF RESIDUES DERIVING FROM THE SYNTHESIS OF CHLORINATED HYDROCARBONS

The present invention relates to a process for disposing of the residues deriving from facilities for the synthesis of chlorinated hydrocarbons.

In particular, the novel process according to the present invention consists of precipitating off, by means of the addition of an alkanol, the low-boiling (i.e., light) components, which are sent to further uses, from the carbonaceous and polymeric solid matter, which is then submitted to pyrolysis, in order to isolate a coal with an extremely low chlorine content, and recover a fraction constituted by chlorinated compounds.

All of the processes for producing chlorinated hydrocarbons lead to the formation of residues, consisting of a liquid fraction and a solid fraction: in general, the components of these mixtures are high-molecular-weight and low-molecular-weight polychlorinated aliphatic and aromatic products, oligomeric and polymeric products with a partially pitch-like consistency, inorganic compounds, catalyst particles and elemental carbon. These byproducts are removed from the processes of synthesis of chlorinated hydrocarbons in mixture with low-boiling constituents, in which they are partially soluble, with the residual, non-soluble portion thereof remaining in said low-boiling constituents in suspended form.

Should these mixtures be concentrated in order to recover the low-boiling components which can be used again, the precipitation would be caused of this suspended solid matter, with a viscous, or even solid, residue, being formed, which would cause considerable problems.

Besides the economic problems of financial character relevant to the recovery of most volatile components with an easily handled residue being simultaneously obtained, there are environmental problems relating to the disposal of these residues, which latter problems are becoming more and more important.

To date, the processes used for this purpose are problematic, or are not completely satisfactory.

For example, these mixtures are stored in desert sites, or at the bottom of the sea. As an alternative, they can be burnt on the high sea, on purposely equipped vessels, so as to minimize the environmental damages caused by hydrogen chloride developed during the combustion.

In this regard, an improvement proposed by DT-AS-1,228,232 consists of absorbing hydrochloric acid as soon as it is formed. The larger the content of suspended solids, the more difficult the application of this kind of method, in that during the combustion, a large amount of pitch-like deposits will be formed.

In GB 1,555,084 a method is disclosed for processing residues deriving from the synthesis of chlorinated hydrocarbons, in particular of vinyl chloride, and containing solid matter, in order to yield organic constituents which can be recycled, hydrogen chloride and coal with a content of 10% of chlorine, which is disposed of by combustion.

The method consists of concentrating the residue under mild conditions in order to separate an as large an amount as possible of low-boiling organic consituents, and in decomposing the so obtained concentrate at a high temperature, under an inert atmosphere, with, on the one hand, a distilled organic fraction, and on the other hand, a carbonaceous residue with a content of 10% of chlorine, being collected.

The concentration of the residue is accomplished by means of thin-film evaporators, under mild conditions, in order to prevent the highly chlorinated hydrocarbons, such as 1,1,2-trichloroethane, from undergoing cleavage, which would generate incrustations. The concentrate which remains on the bottom of these evaporators after the stripping treatment contains all of the reaction byproducts suitably diluted with a still fairly large amount of light byproducts, so as to give said residue a viscosity value of from 10 to 15 centipoises.

Such a viscosity value appears to be essential in order to make possible the recovery of the concentrate from the bottom of the evaporators and of the transfer of said concentrate to the successive pyrolysis step to be carried out.

The pyrolysis is accomplished inside an auger furnace at temperatures preferably comprised within the range of from 270° C. to 330° C. Higher temperature would cause the organic, distillable fraction to decompose, with huge amounts of hydrogen chloride being produced.

In order to avoid this drawback, the process is carried out according to GB 1,555,084, but by working at a compromise temperature, which unfortunately leaves a non-decomposed amount of the heavy or polymeric components, which is then found in the residual carbonaceous matter, and is the cause of the high chlorine content thereof.

The present Applicant has now found a process for the treatment of the chlorinated pitches deriving from the synthesis of chlorinated hydrocarbons, according to which process the separation by precipitation is of the polymeric portion and of the carbonaceous matter caused by adding an alcohol. These solid materials are removed by decantation, and are then submitted to a pyrolysis, whilst the liquid fraction of byproducts is recovered by distilling off the alcohol and submitting the distillation residue to a subsequent rectification in order to recover the re-useable products.

Compared to the processes known from the prior art, the process according to the present invention possesses the advantage that carbonaceous material with an extremely low chlorine content is isolated, and from a general viewpoint, is a process which can be used for the treatment of a wide range of chlorinated pitch compositions.

In particular, the process consists of a first step in which the chlorinated pitches are submitted to distillation under reduced pressure, comprised within the range of from 60 to 80 torr, and at a temperature comprised within the range of from 60° C. to 120° C., until a viscosity not higher than 800 cst at 25° C. is obtained, in order to recover from 10 to 20% of the product fed to said distillation.

The distillate is directly recycled to an oxychlorination reactor.

The distillation residue is then mixed in the second step with an alcohol selected from among methanol, ethanol or propanol, in an amount comprised within the range of from 10% to 40% by weight, and the so obtained slurry is transferred to a decanter. At the end of the decantation step, the supernatant is separated from the settled solid phase.

The precipitate is further treated with an amount of fresh alcohol comprised within the range of from 10% to 40% of the same precipitate, and the suspension is decanted again.

The mother liquors which are obtained from this third step are combined with those which derive from the preceding step, and are distilled. In that way, the alcohol is recoved and is then recycled to the process, whilst the residue is evaporated and is submitted to a separation in a distillation tower.

A fraction is recovered which is fed to the oxychlorination, and from the bottom an aliquot of heavy materials (such as, e.g., hexachlorobutadiene, hexachlorobenzene) is drawn and is disposed of by incineration.

The solid phase obtained at the end of the third step still contains chlorinated aliphatic and aromatic hydrocarbons together with the alcohol, but is mainly constituted by carbonaceous materials, polymeric materials and inorganic compounds.

These solid materials are fed to an auger furnace heated at a temperature comprised within the range of from 300° to 500° C. During the pyrolysis a small amount of HCl is developed, and a distilling fraction is collected; at the end of this fourth step from the bottom of the auger furnace a carbonaceous solid is collected, which contains a rather small amount of chlorine, i.e., an amount of chlorine comprised within the range of from 0.5 to 5%.

This low-chlorine carbonaceous material can be easily disposed of by combustion.

The fraction distilled during the pyrolysis is submitted to the same treatment as previously disclosed for the alcoholic solutions of mother liquors.

In comparison to the processes according to the prior art, according to the present invention, the instant Applicant succeeds in disposing of pitches of various compositions, having high viscosities, even higher than 35 cP.

In fact, the steps of extraction and decantation employed in the present invention do not suffer from the limitations and problems which characterize the use of such delicate equipment as thin-film evaporators, in order to process pitch-like mixtures.

According to the present process, most chlorinated light compounds can be removed from the residue by means of the treatment with an alcohol before said residue is submitted to the step of pyrolysis. Therefore, solid material is pyrolized. This material is mainly composed of carbonaceous and polymeric materials, and inorganic compounds. This solid material can be pyrolysed at a high temperature without large amounts of hydrogen chloride being developed. Simultaneously, coal with an extremely small content of chlorine an be isolated.

EXAMPLE 1

163 g of a mixture of chlorinated pitches having a density of 1.4, containing $C_1$ halogenated compounds, saturated and unsaturated $C_2$–$C_5$ chlorocarbons, chlorinated and chlorine-free aromatic compounds, polymers, and coal, is charged to a distiller, and is heated up to 90° C. under a pressure of 60 torr. From the head of the column, 33 g of distillate is collected, and is fed to the oxychlorination reactor.

To the residue (130 g) 55 g of methanol is added: 185 g is obtained of a slurry which is allowed to decant (decantation speed: 10 cm/hour). 104.7 ml of an alcoholic solution (d =0.95) is separated, and from it 73.4 g of chlorinated compounds is obtained by distillation. From the bottom of the decanter 71 g is obtained of a suspension which has a density of 1.21.

To this suspension a further 30 g of fresh methanol is added, the resulting mixture is stirred and is allowed to decant again. The mother liquors from this second extraction contain 18.3 g of chlorinated compounds, which are recovered by distillation. The decanted solids are charged to an auger furnace and are pyrolysed at 450° C. 17 g of methanol and 26.3 g of chlorinated compounds distil off and at the end of the pyrolysis 12 g of coal with a content of 0.5% of chlorine is recovered.

We claim:

1. A process for disposing of chlorinated pitches derived from the synthesis of chlorinated hydrocarbons, wherein said pitches contain suspended solid matter and yield a solid or viscose deposit when low-boiling components thereof are removed by distillation, consisting of:

treating said chlorinated pitches twice in succession with an alcohol to precipitate solid matter;

removing said solid matter by decantation;

pyrolizing said solid matter; and distilling the combined supernatants which remain after dectantation of said solid matter in order to recover said alcohol, which is recycled to the process; and submitting the distillation residue to a subsequent rectification in order to recover reusable products.

2. The process of claim 1, wherein said chlorinated pitches derive from the synthesis of vinyl chloride from 1,2-dichloroethane by thermal splitting.

3. The process of claim 1, wherein said chlorinated pitches, before said treating with said alcohol, are stripped at a temperature within the range from 60° C. to 120° C. under pressure within the range from 60 to 80 torr until a viscosity not higher than 800 cst at 25° C. is obtained.

4. The process of claim 1, wherein said alcohol is selected from the group consisting of methanol, ethanol, and propanol.

5. The process of claim 4, wherein said alcohol is methanol.

6. The process of claim 1, wherein the amount of alcohol used in each successive treatment is within the range from 10% to 40% by weight of said chlorinated pitches.

7. The process of claim 1, wherein said pyrolizing is carried out inside an auger furnace at a temperature within the range from 300° C. to 500° C.

8. The process of claim 3, wherein said temperature is 90° C. and said pressure is 60 torr.

9. The process of claim 3, wherein the resulting distillate is collected and fed to an oxychlorination reactor.

10. The process of claim 7, wherein said pyrolizing is carried out at a temperature of 450° C.

* * * * *